(12) United States Patent
Abraham et al.

(10) Patent No.: US 6,572,847 B2
(45) Date of Patent: Jun. 3, 2003

(54) ELIMINATION OF ODORS FROM LUBRICANTS BY USE OF A COMBINATION OF THIAZOLES AND ODOR MASKS

(75) Inventors: William D. Abraham, South Euclid, OH (US); James P. Roski, Wickliffe, OH (US); Jerry L. Rutter, Mentor, OH (US); Craig D. Tipton, Perry, OH (US); Victor A. Gober, Novelty, OH (US); James J. Schwind, Chardon, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 36 days.

(21) Appl. No.: 09/817,620

(22) Filed: Mar. 26, 2001

(65) Prior Publication Data

US 2001/0051594 A1 Dec. 13, 2001

Related U.S. Application Data

(60) Provisional application No. 60/193,913, filed on Mar. 31, 2000.

(51) Int. Cl.$^7$ ............................... C10L 1/24; A61L 9/01
(52) U.S. Cl. ...................... 424/76.21; 424/76.1; 44/341
(58) Field of Search ........................... 44/341; 424/76.1, 424/76.21

(56) References Cited

U.S. PATENT DOCUMENTS

| 2,145,971 | A | | 2/1939 | Cantrell et al. | 87/9 |
|---|---|---|---|---|---|
| 3,005,778 | A | | 10/1961 | Sweetman | 252/170 |
| 3,658,708 | A | | 4/1972 | Ratto | 252/56 R |
| 3,752,766 | A | | 8/1973 | Wilson | 252/57 |
| 3,940,408 | A | * | 2/1976 | Waldbillig | 260/306.8 |
| 3,940,409 | A | * | 2/1976 | Waldbillig | 260/306.8 |
| 4,130,562 | A | | 12/1978 | Dubs et al. | 260/302 |
| 4,216,100 | A | * | 8/1980 | Yaffe | 252/46.7 |
| 4,315,889 | A | | 2/1982 | McChesney et al. | 442/7 |
| 4,555,352 | A | * | 11/1985 | Garner et al. | 252/35 |
| 5,014,033 | A | | 5/1991 | Jay et al. | 336/94 |
| 5,318,712 | A | * | 6/1994 | Lange et al. | 252/47.5 |
| 5,516,440 | A | * | 5/1996 | Dasai et al. | 252/32 |
| 5,559,271 | A | * | 9/1996 | Shaw et al. | 568/21 |
| 5,653,787 | A | * | 8/1997 | Poirier | 44/341 |
| 6,028,210 | A | * | 2/2000 | Watts et al. | 558/287 |

FOREIGN PATENT DOCUMENTS

| EP | 0 976 726 A1 | 2/2000 |
|---|---|---|
| JP | 61203199 | 9/1986 |

* cited by examiner

*Primary Examiner*—Barbara P. Badio
(74) *Attorney, Agent, or Firm*—David M. Shold; Michael F. Esposito

(57) ABSTRACT

The objectionable odors generated from lubricants is minimized by including in said lubricant a thiazole compound and grape odor mask.

20 Claims, No Drawings ific application, materials such as detergents, dispersants, antioxidants, antiwear agents, extreme pressure agents, rust inhibitors, corrosion inhibitors, foam inhibitors, seal swell agents, surface active agents, and friction modifiers.

ELIMINATION OF ODORS FROM LUBRICANTS BY USE OF A COMBINATION OF THIAZOLES AND ODOR MASKS

This application claims priority from U.S. Provisional Application 60/193,913, filed Mar. 31, 2000.

BACKGROUND OF THE INVENTION

The present invention relates to reducing or eliminating objectionable odors from industrial or transportation fluids by use of a combination of thiazoles and odor masks.

Industrial and transportation fluids include lubricants for automotive crankcase application and driveline applications such as engine oils, gear oils, transmission fluids, and farm tractor fluids, as well as a variety of other fluids including hydraulic fluids, greases, axle lubricants, metal-working fluids. Such lubricants and fluids necessarily serve multiple functions. Among these are lubrication of the parts in which they come in contact, prevention of wear and corrosion, and prevention of the harmful effects of oxidation or contamination from engine combustion products or other sources. Modern fluids of this type can contain a multitude of well-known additives, including, depending on the specific application, materials such as detergents, dispersants, antioxidants, antiwear agents, extreme pressure agents, rust inhibitors, corrosion inhibitors, foam inhibitors, seal swell agents, surface active agents, and friction modifiers.

Industrial and transportation fluids must not only meet the technical requirements of such applications. They must also be compatible with the needs and sensibilities of workers and other personnel who encounter these fluids either in their end-use application or in handling, transportation, or storage activities. Sometimes various of the additive components can generate offensive odors, which can be apparent upon opening a container of the fluid prior to its use, or during use of the fluid, particularly when the use involves operating or handling at elevated temperatures.

One application in which odor generation has been a particular problem is in open crankcase diesel engines for trucks. Such engines are characterized by an open crankcase, that is, one in which the air from within the engine block which has been in contact with the oil is not passed through the exhaust system but ventilated more or less directly into the atmosphere. Typically, a breather tube emerges from the top of the rocker cover or some other elevated point of the engine block. Within the tube there is sometimes a metal mesh to retain oil mist and condensate, but to permit venting of the air to a location relatively near the engine, either under the hood or behind the cab. In some designs the vent is near the passenger cab ventilation air intake, with the result that fumes can enter the passenger compartment.

Moreover, engine oils in general are distinct from other lubricants such as transmission fluids in that they are exposed to exhaust gases and generally more rigorous environments. These factors may exacerbate odor problems.

A variety of chemical sources can be responsible for offensive odors, amine-containing materials and sulfur-containing compounds being principal offenders. Among the specific materials which are believed to contribute to odor formation are sulfurized alkyl-substituted phenates, sulfurized olefins, phosphorus-sulfur agents such as amine salts of trialkyldithiophosphate ester-substituted phosphates, amine-containing dispersants such as succinimide dispersants, amine-containing surface active agents such as fatty imidazolines and alkoxy-lated fatty amines, amine-containing dispersant viscosity modifiers, other phosphorus-containing materials, and alcohols such as $C_3$ to $C_{12}$ alcohols, especially C4 to $C_9$ alcohols. While such materials may or may not in themselves have objectionable odors, they may also interact with other components of the fluid, particularly at elevated temperatures, in ways which are not particularly well characterized. Thus complicated odors may arise which may not be directly traceable to a particular source. In some cases it is simply difficult or impossible to identify the chemical source of the odor.

It is well known, however, that certain of these materials can generate odors which can be detected at ambient air concentration levels far below those levels which may cause concerns from a health or safety standpoint. Accordingly, there is a need effectively reducing or neutralizing such odors without adversely affecting the functional performance of the fluid which is treated.

It is known that certain odors or fragrances can disguise or mask objectionable odors or even minimize their subjective sensation. A number of products are commercially available for this purpose, which can be used as additives for industrial or transportation fluids. However, in many cases one odor is merely replaced by another, leading to an objectionably strong floral or fruity scent. Complete elimination of the offensive odor remains, in many instances, problematical, especially since odor is a subjective human perception.

U.S. Pat. No. 5,318,712, Lange et al., Jun. 7, 1994, discloses a composition of a major amount of an oil of lubricating viscosity and a minor amount of a reaction products of at least one dimercaptothiadiazole and at least one alpha,beta unsaturated ester. The invention also includes aqueous compositions. Water-based functional fluids can optionally include other conventional additives such as odor masking agents.

SUMMARY OF THE INVENTION

The present invention, therefore, provides a method for minimizing the perception of odors generated from lubricants such as industrial or transportation fluids, comprising including in said fluid a thiazole compound represented by the structure

where each R is independent H or a hydrocarbon group, provided that at least one R is a hydrocarbon group; each n is independently 1 or 2, and TZ represents a thiazole nucleus; and an odor mask.

The present invention further provides a lubricant (such as an industrial or transportation fluid) which contains such a thiazole compound and an odor mask, whereby objectionable odors are minimized.

DETAILED DESCRIPTION OF THE INVENTION

Various preferred features and embodiments will be described below by way of non-limiting illustration.

While not an essential component for the generation or elimination of odors, many industrial or transportation fluids include an oil of lubricating viscosity. Such oils are well known and include natural and synthetic lubricating oils and mixtures thereof.

Natural oils include animal oils, mineral lubricating oils, and solvent or acid treated mineral oils. Synthetic lubricating oils include hydrocarbon oils (polyalpha-olefins), halo-substituted hydrocarbon oils, alkylene oxide polymers, esters of dicarboxylic acids and polyols, esters of phosphorus-containing acids, polymeric tetrahydrofurans and silicon-based oils.

The oil of lubricating viscosity can be selected to provide lubricating compositions with a kinematic viscosity of at least 3.5 or 4.0 cSt at 100° C. In one embodiment, the lubricating compositions have an SAE gear viscosity grade of at least SAE 75W. The lubricating composition may also have a so-called multigrade rating such as SAE 75W-80, 75W-90, 75W-140, 80W-90, 80W-140, 85W-90, or 85W-140. For crankcase lubricants multigrade ratings such as 0W-30, 5W-30, 5W-40, 10W-40, 15W-40 and the like are common. Multigrade lubricants commonly include a viscosity improver which is formulated with the oil of lubricating viscosity to provide the above lubricant grades. Viscosity modifiers are typically polymers and are well known to those skilled in the art of lubricants and need not be described in further detail.

The odor reduction compositions and methods of the present invention are particularly useful in those oils which are designated as API (American Petroleum Institute) Group II, Group III, and Group IV base oils, and mixtures thereof. While not intending to be bound by any theory, it is believed that the higher amount of unsaturated materials ($\geq 10\%$) present in API Group I base oils may react with odor-causing components and to some extent neutralize the odors, even without the treatment of this invention. The lower amounts of unsaturation (<10%) present in the higher grade base oils, on the other hand, may lead to increased severity of odor problems, which can be solved by the present invention.

In a similar way, it is believed that the present invention is particularly useful in low chlorine lubricant compositions. Low chlorine compositions are those which contain less than 150 parts per million chlorine, and preferably less than 100, 50, or 10 parts per million chlorine in the final formulation. The chlorine will typically appear bound as a chlorine substituent in one or more of the additives in the lubricant. Chlorine is commonly used in the manufacturing of dispersants, and, in particular, in the synthesis of the non-polar hydrocarbon chain present in certain dispersants. A certain low level of chlorine is typically retained within such dispersants. Again without intending to be bound by any theory, it is believed that such molecules may undergo dehydrochlorination to provide unsaturated species which may subsequently react with odor causing materials as described above. This mechanism is not available in the absence of chlorine containing components; hence, the present invention is particularly desirable in low chlorine formulations. There are many methods known in the art for preparing low chlorine dispersants, one of which is disclosed in U.S. Pat. No. 6,077,909.

The first compound which serves as the odor modifier is a thiazole compound. Thiazoles are compounds which contain both a sulfur atom and a nitrogen atom in a ring. The term "thiazole" is thus used herein generically to encompass both thiazoles proper, that is, materials containing one nitrogen and one sulfur atom in the ring, as well as thiadiazoles, that is, materials containing sulfur and two nitrogen atoms in the ring. One type of thiazole, then, is the benzothiazoles and substituted benzothiazoles, that is, compounds having the general structure,

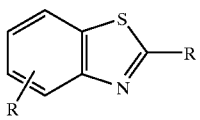

where R is an optional substituent, described in greater detail below.

Another type of thiazole compound is the thiadiazoles. Thiadiazoles can generally have any of the following nuclear structures:

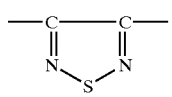

1

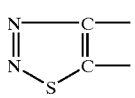

2

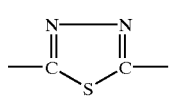

3 the third of which being the most important. The thiadiazoles of the present invention generally have the structure

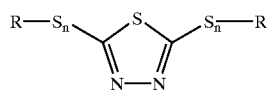

where n is typically 1 or 2.

Unsubstituted thiazoles, that is, in which all R groups are hydrogen, are of only limited practical applicability because of generally insufficient solubility in lubricating oils or other practical media. The R groups, therefore, are typically hydrocarbon groups (e.g., alkyl, aryl, or mixed alkyl and aryl) of sufficient length to provide the compounds with a measure of oil solubility. When two or more R groups are present in a single compound, the total number of carbon atoms should be sufficient to provide the compound with such solubility. Generally, each R group will have 1 to 50 carbon atoms, and in other embodiments 1 to 30, or 1 to 18, or 1 to 12, or 1 to 8 carbon atoms. Examples of R groups that can be used include methyl, ethyl, propyl, isopropyl, butyl, n-butyl, isobutyl, amyl, 4-methyl-2-pentyl, ethyl hexyl, octyl, isooctyl, nonyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl, alkylnaphthylalkyl, and mixtures thereof.

The thiadiazoles are generally prepared by oxidative reaction of unsubstituted dimercaptothiadiazole with an alkyl mercaptan in the presence of hydrogen peroxide. The product can contain at least a certain amount of a mono-substituted material of the general structure

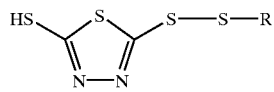

where R can be a $C_6$ to $C_{12}$ alkyl group. The amount of alkyl mercaptan component is generally limited so that the product is a mixture of about 85% of the di-substituted material and about 15% of the monosubstituted material.

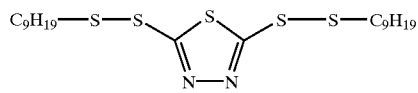

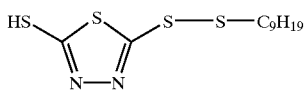

In the above mixture, which is preferred, one preferred R group being a nonyl group is illustrated. Other preferred groups include octyl groups.

The amount of the thiazole compound in the final formulation is typically 50 to 5000 parts per million by weight. Higher concentrations, such as 1000 to 3000 or 5000 ppm, or 1300 to 2000 ppm, are characteristic of gear oil formulations, while relatively lower concentrations of 50 to 1000 parts per million by weight, preferably 100 to 800 ppm, 200 to 600 ppm, or most preferably about 300 ppm, that is, 250 to 400 ppm, are characteristic of engine oil or transmission fluid applications. Higher concentrations would be generally employed in the gear oil formulations since it is believed that those fluids contain higher concentrations of odor forming materials, and this is one feature which distinguishes gear oils from engine oils and transmission fluids. If the thiazole compound is supplied as a concentrate, its concentration will be correspondingly higher, for instance, by one or two orders of magnitude. Likewise, the thiazole compound can also be present in higher concentrations if it is intended to perform an additional function within the fluid, for which higher concentrations are desired.

The other important component is a fragrance or odor mask, also referred to as an odorant, of which many types are commercially known and available from such sources as PMC Specialties, Alpine Aromatics, or Haarmann & Reimer (a Bayer company). The chemical structures of such odor masks, which may be mixtures, are not always readily available, but many of them are believed to include relatively simple aromatic esters such as methyl benzoate and, in particular, homologues thereof such as ring alkyl-substituted methyl benzoates, e.g., o- or p-methyl methyl benzoate. A wide variety of fragrances are commercially available, with diverse descriptions such as bubble gum, cherry, citrus, concord (grape), fresh air, grape, lemon, pine, "Pine-sol"™, root beer, sassafras, spice, tutti fruitti, vanilla, and wintergreen. Among the preferred and more effective scents are those known as Kompensol™ D61186T, from Haarmann & Reimer (a "Pine-sol" or spice odor), Cobratec Fresh Air™ from PMC Specialties, and Cobratec Cool Concord™ (a grape odor) from PMC Specialties, and a similar grape odor from Alpine Aromatics. Another list of odor masking compound is found in U.S. Pat. No. 5,559,271, Shaw et al., Sep. 24, 1996. The materials disclosed therein fall into the group consisting of wintergreen, cinnamons, vanillins, terpenes, sesquiterpenes, and combinations thereof.

The foregoing odor masks may be used singly or in combination. A combination of grape and "fresh air" has proven particularly effective in certain applications, where it was found that the use of the grape odor mask as the only odor mask sometimes resulted in a faint residual sweet odor.

The amount of the odor mask, when used in combination with the thiazole compound, can be effective at surprisingly low concentrations, such as 0.1 to 500 parts per million. (The concentration ranges used herein are based on the chemical as commercially supplied. To the extent that the commercial material contains any diluent, the amount of active chemical will be proportionally reduced. It is believed that in many instances this is the case, and the amount of the active ingredient in an odor mask may be as little as 1% of the total commercial material. Accordingly, if one were to deal with chemically pure components, the amounts employed should be adjusted accordingly. Such adjustments are within the abilities of the person skilled in the art.) The higher ranges, of 50 to 500 ppm, preferably 100 to 300 ppm, or 150 to 250 ppm, can be employed in gear oil applications, consistent with the use of higher concentrations of thiazole and larger amounts of odor causing chemicals. Lower ranges, 0.1 to 50 ppm, preferably 15–20 or 1–10, 2–8, or 3–5 ppm have been found to be effective in engine oil and transmission fluid applications, particularly when the odor mask is grape or a combination of grape and "fresh air." Under favorable conditions, such low concentrations, in combination with the thiazole, can completely neutralize a sulfur or amine odor. If two or more odorants are used, the total concentration of the multiple odorants can be within the above ranges or may be slightly higher. If the odor mask is provided in a concentrate, once again the concentration supplied will be correspondingly higher, e.g., by one or two orders of magnitude.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not susceptible of easy description. Nevertheless, all such modifications and reaction products are included within the scope of the present invention; the present invention encompasses the composition prepared by admixing the components described above.

EXAMPLES

The odor reduction from an open crankcase diesel engine is investigated using the following procedure:

1. A diesel truck is slightly altered to accentuate the permeation of crankcase odor into the cab via clamping one of the two breather tubes located near the cab venting system and removing the seal strippings around the vent area.
2. Fresh candidate oil is charged into a new filter and the truck at the beginning of each day.
3. The truck is allowed to fully warm up by idling for 10 minutes.
4. When the truck is warm—as indicated by the temperature gauge—several individuals are picked up and carried within the cab.
5. The truck is driven at highway speeds, i.e., 105 to 120 km/hr (65 to 75 m.p.h.) roughly 5.6 km (3.5 miles) on a limited access highway with no heat, air conditioning, or fan, with the vents open.
6. After exiting the highway, the truck is pulled to the side of the road, stopped completely, and the fan turned on at high speed to force air through the vents so any odors from the engine compartment will be detected in the cab.
7. After checking for odors and rating the candidate oil, the truck is driven back to its garage by the same route—often in overdrive "off" position for maximum rpm—and again with no heat or air conditioning, vent position closed and fan off.
8. Upon reaching its garage, the truck is stopped outside the garage and the vents and fan are turned on at high airflow for further evaluation of odors entering the cab.

At this time, the hood of the truck is opened so the odors coming from the engine compartment as well as from the engine itself can be investigated. The oil filter cap is momentarily removed and sniffed at this time to evaluate odors from the warm engine oil.

9. The truck was returned to its garage after the second evaluation and the warm oil is completely drained from the engine as quickly as possible. A four-ounce sample of used oil is taken at about mid-oil change for further testing and odor evaluation.

10. Upon complete draining of the oil (roughly 10 to 15 minutes) and removal of the former oil filter, a fresh oil filter containing the next sample is affixed to the engine, and the crankcase is filled with the next candidate oil. Because the engine is already warm and the candidate oil is at room temperature, approximately 5 to 8 minutes of idling with each candidate sample is sufficient to bring the truck to test temperature.

The above-described test is carried out within 45 minutes for each sample, allowing evaluation of 8 to 9 candidates per day.

The oils used for testing contain a standard lubricating base oil containing a commercial diesel engine lubricant additive package, including sulfurized ester, sulfurized olefin, and sulfur-coupled phenate detergent.

Each oil is evaluated as described above for objectionable odor and is rated on a scale from A to D-, where A is the best indicating no or only a trace of sulfur odor (and other objectionable odors, such as alcohol odor) in the truck cab. Results are shown in the Table I:

TABLE I

| Example No. | Added components[a] | Amount (ppm) | Rating |
|---|---|---|---|
| 1 (baseline) | none | 0 | C+, B (2 runs) |
| 2 | ortho-vanillin | 500 | D |
| 3 | diC$_9$dimercaptothiadiazole | 600 | A– to B+ |
| 4 | Concord grape mask | 10 | B |
| 5 | diC$_9$dimercaptothiadiazole Concord grape mask | 310 10 | A |
| 6 | diC$_9$dimercaptothiadiazole "Fresh Air" mask | 310 25 | A to A– |
| 7 | diC$_9$dimercaptothiadiazole wintergreen mask | 310 25 | A– to B+ |
| 8 | diC$_9$dimercaptothiadiazole Concord grape mask | 455 5 | A |
| 9 | diC$_9$dimercaptothiadiazole Concord grape mask | 160 5 | A– to B+ |

In all instances, the di-C$_9$-dimercaptothiadiazole is a mixture of about 85% of the di-C$_9$ material and about 15% of the mono-C$_9$ material.

In all instances, the di-C$_9$-dimercaptothiadiazole is a mixture of about 85% of the di-C$_9$ material and about 15% of the mono-C$_9$ material.

A similar set of tests is run on a similar base formulation, providing the results in Table II:

TABLE II

| Example | Added components | Amount (ppm) | Comments |
|---|---|---|---|
| 10 | diC$_9$dimercaptothiadiazole | 310 | Some sulfur (fail) |
| 11 | diC$_9$dimercaptothiadiazole "fresh air" | 310 25 | Trace sulfur (better but insufficient) |
| 12 | diC$_9$dimercaptothiadiazole grape | 310 5 | No sulfur, slight sweet |
| 13 | diC$_9$dimercaptothiadiazole grape | 310 1 | No sulfur, slight sweet |

TABLE II-continued

| Example | Added components | Amount (ppm) | Comments |
|---|---|---|---|
| 14 | diC$_9$dimercaptothiadiazole grape | 310 2 | No sulfur, slight sweet |
| 15 | diC$_9$dimercaptothiadiazole grape | 310 3 | No sulfur, no sweet |
| 16 | diC$_9$dimercaptothiadiazole grape "fresh air" | 310 2 10 | No sulfur, no sweet. |

Example 17.

To a fully formulated automatic transmission fluid which contains about 300 parts per million di-C$_9$-dimercaptothiadiazol mixture is added 5 parts per million of a pine/spice odor mask. The resulting mixture exhibits an acceptable odor.

Examples 18–25.

To a fully formulated axle lubricant which contains di-C$_9$-dimercaptothiadiazole mixtures in the amount shown in Table III is added grape odor mask in the amount shown. The resulting mixture will exhibit an acceptable odor.

TABLE III

| Example | diC$_9$dimercaptothiadiazole, % | grape odor mask, ppm |
|---|---|---|
| 18 | 0.10 | 200 |
| 19 | 0.15 | 200 |
| 20 | 0.20 | 150 |
| 21 | 0.20 | 200 |
| 22 | 0.20 | 250 |
| 23 | 0.25 | 200 |
| 24 | 0.35 | 200 |
| 25 | 0.50 | 200 |

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, except in the case of commercial odor maskants or unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A method for minimizing odors generated from lubricants, comprising including in said lubricant:

(a) a thiazole compound represented by the structure

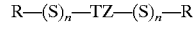

R—(S)$_n$—TZ—(S)$_n$—R where each R is independent H or a hydrocarbon group, provided that at least one R is a hydrocarbon group;

each n is independently 1 or 2, and the TZ represents a thiazole nucleus; and (b) about 1 to about 10 parts per million of grape odor mask.

2. The method of claim 1 wherein the thiazole compound comprises a dimercaptothiadiazole.

3. The method of claim 2 wherein the thiazole compounds comprises a material represented by the structure

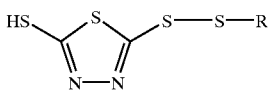

where R is a $C_6$ to $C_{12}$ alkyl group.

4. The method of claim 2 wherein the thiazole compound comprises a mixture of materials represented by the following structures:

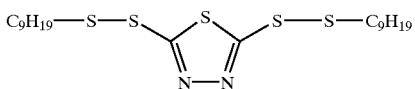

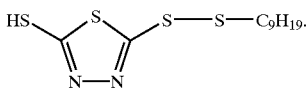

5. The method of claim 1 wherein the amount of the thiazole is about 50 to about 5000 parts per million by weight.

6. The method of claim 1 wherein the amount of the thiazole is about 1300 to about 2000 parts per million by weight.

7. The method of claim 1 wherein the amount of the thiazole is about 100 to about 800 parts per million by weight.

8. The method of claim 1 wherein the composition further comprises a sulfur-containing compound, said sulfur-containing compound being associated with said objectionable odor.

9. The method of claim 1 wherein the lubricant comprises an oil of lubricating viscosity selected from the group consisting of API Group II, Group III, and Group IV base oils, and mixtures thereof.

10. The method of claim 1 wherein the lubricant contains less than about 150 parts per million by weight chlorine.

11. The method of claim 1 wherein the lubricant is an engine lubricant.

12. The method of claim 1 wherein the lubricant is a diesel engine lubricant.

13. The method of claim 1 wherein the lubricant is a gear oil.

14. The method of claim 1 wherein the lubricant is a transmission fluid.

15. A lubricant having a reduced level of objectionable odor, comprising:

(a) a thiazole compound represented by the structure

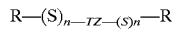

where each R is independent H or a hydrocarbon group, provided that at least one R is a hydrocarbon group; each n is independently 1 or 2, and TZ represents a thiazole nucleus;

(b) about 1 to about 10 parts per million of grape odor mask; and (c) an oil of lubricating viscosity.

16. A composition prepared by admixing the components of claim 15.

17. The lubricant of claim 15 wherein the thiazole compound thiazole comprises a material represented by the structure

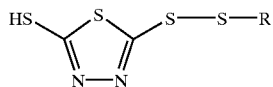

where R is a $C_6$ to $C_{12}$ alkyl group.

18. The lubricant of claim 15 wherein the amount of the thiazole compound is about 50 to about 5000 part per million.

19. The lubricant of claim 15 wherein the oil of lubricating viscosity is selected from the group consisting of API Group II, Group III, and Group IV base oils and mixtures thereof.

20. The lubricant of claim 15 wherein the lubricant contains less than about 150 parts per million by weight chlorine.

* * * * *